United States Patent [19]

Youngner et al.

[11] Patent Number: 5,149,531
[45] Date of Patent: Sep. 22, 1992

[54] METHOD OF USING COLD-ADAPTED LIVE INFLUENZA VIRUS VACCINE AS AN ANTIVIRAL AGENT AGAINST INFLUENZA

[75] Inventors: Julius S. Youngner; Patricia W. Dowling, both of Pittsburgh, Pa.

[73] Assignee: University of Pittsburgh of the Commonwealth System of Higher Education, Pittsburgh, Pa.

[21] Appl. No.: 544,823

[22] Filed: Jun. 27, 1990

[51] Int. Cl.$^5$ .................. A61K 39/149; A61K 39/12
[52] U.S. Cl. .......................................... 424/89
[58] Field of Search ...................................... 424/89

[56] References Cited

U.S. PATENT DOCUMENTS 4,552,758 11/1985 Murphy et al. ................ 424/89

OTHER PUBLICATIONS

Clements et al., The Lancet, (Mar. 31, 1984), pp. 705–708.
Monto et al., The J. of Infect. Dis., vol. 145, No. 1, Jan. 1982, pp. 57–64.
Maassab, Adaptation and Growth Characteristics of Influenza Virus at 25° C., Nature, Feb. 11, 1967, pp. 612–614.
Maassab, Biologic and Immunologic Characteristics of Cold-Adapted Influenza Virus, Jour. of Immunology, vol. 102, No. 3, pp. 728–732 (1969).
Murphy et al., Infec. Immun. 29, pp. 348–355 (1980).
Maassab et al., Evaluation of a Cold-Recombinant Influenza Virus Vaccine in Ferrets, Journal of Infectious Diseases, vol. 146, No. 6 (Dec. 1982).
Cox et al., Virology, 167, pp. 554–567 (1988).
Clements et al., Resistance of Adults to Challenge with Influenza a Wild-Type Virus After Receiving Live or Inactivated Virus Vaccine, Journal of Clinical Microbiology, vol. 23, No. 1, pp. 73–76 (1986).
Snyder et al., Journal of Virology, 62, pp. 488–495 (1988).
Whitaker Dowling et al., Dominance of Cold-Adapted Vaccine Strains of Influenza a Viruses etc., Genetics and Pathogenicity of Nagative Strand Viruses, Elsevier pp. 402–407 (1989).

*Primary Examiner*—Merrell C. Cashion, Jr.
*Assistant Examiner*—Choon Koh
*Attorney, Agent, or Firm*—Arnold B. Silverman

[57] ABSTRACT

A method of treating a patient for having influenza includes introducing intranasally into said patient a prophylactically or therapeutically effective dosage of an attenuated reassortant live influenza virus as an antiviral agent and effecting by said introduction immediate interference with the growth of said influenza virus.

15 Claims, No Drawings

METHOD OF USING COLD-ADAPTED LIVE INFLUENZA VIRUS VACCINE AS AN ANTIVIRAL AGENT AGAINST INFLUENZA

GOVERNMENT RIGHTS

This invention was made with Government support under the Department of Health and Human Services, National Institutes of Health, National Institute of Allergy and Infectious Diseases Grant No. AI06264. The Government has certain rights in the invention.

BACKGROUND OF THE INVENTION

1. Field of the Invention

This invention relates to a method of treating influenza and, more specifically, it relates to introducing intranasally into a patient a prophylactically or therapeutically effective dosage of an attenuated live influenza virus to effect immediate interference with the growth of said influenza virus.

2. Description of the Prior Art

Influenza is currently the sixth leading cause of death in the United States. Particularly vulnerable are the very old and very young which have a higher than average influenza mortality rate.

As influenza epidemics and pandemics can be extremely devastating, particularly in high risk populations, such as retirement communities for senior citizens and daycare centers caring for infants, prompt action to attack the virus is critical. Unfortunately, conventional vaccines for influenza require about two weeks to cause the body's immune system to build up enough antibodies to produce immunity.

As the incubation period for influenza is short, it is critical to have a means of interfering with the growth of the influenza virus within the patient in an immediate manner.

It has been known to produce a cold-adapted influenza virus material derived from an epidemic virus strain. See generally Maassab, Adaptation and Growth Characteristics of Influenza Virus at 25° C., Nature, Feb. 11, 1960, 7, pages 612–614, and Maassab, Biologic and Immunologic Characteristics of Cold-Adapted Influenza Virus, the Journal of Immunology, Vol. 102, No. 3, 1969, pages 728–732. Noted in this prior art is the fact that cold variants of influenza virus showed an impaired capacity to reproduce at acid pH (5.7 to 6.3) and at elevated temperature 41° C. See generally Cox et al. Virology 167, pp. 554–567 (1988) and the ability to grow at 25° C. In the reported tests, these features were used as markers to differentiate the cold variant from the original wild strain. These cold variants were found to elicit good antibody responses in tests with mice, ferrets, and humans.

The advantageous use of live attenuated cold-adapted reassortant influenza A H3N2 and H1N1 virus vaccine against homologous wild-type virus seven months after vaccination has been reported. See Clements et al., Resistance of Adults to Challenge with Influenza A Wild-Type Virus After Receiving Live or Inactivated Virus Vaccine, Journal of Clinical Microbiology, Vol. 23, No. 1., pages 73–76 (1986). These attenuated cold-adapted vaccines produced results at least as great as the inactivated virus vaccines when administered to healthy persons in prophylactic doses.

The inventors of the present invention in September of 1989 reported two cold-adapted reassortants which are candidates for a live influenza A virus vaccine interfering with the replication of their parental wild-type viruses in mixed infections. The cold-adapted reassortant was also found to be able to inhibit heterologous influenza A virus, Whitaker-Dowling and Youngner, Dominants of Cold-Adapted Vaccine Strains of Influenza A Viruses and Mixed Infections with Wild-Type Virus, Genetics and Pathogenicity of Negative Strand Viruses, Elsevier Science Publishers BV, pages 402–407 (1989).

SUMMARY OF THE INVENTION

The present invention has met the above-described need by introducing a prophylactically or therapeutically effective dosage of an attenuated live influenza virus as an antiviral agent into a patient intranasally and, thereby, effecting immediate interference with, or establishing an antiviral state, the growth of said influenza virus without awaiting the generation of sufficient antibodies within the patient to establish immunity to the influenza.

The attenuated virus may be employed in a solution having a concentration of up to about 107 egg infectious doses (EID50) per milliliter with the quantity of solution introduced intranasally being up to about 1 milliliter total solution and the dosage being administered one time.

It is an object of the present invention to provide a method for directly interfering with the development of influenza within a patient without awaiting the generation of a sufficient level of antibodies to establish immunity.

It is a further object of the present invention to employ an attenuated live influenza virus which is introduced intranasally for this purpose.

It is a further object of the invention to provide an effective means for taking immediate action to resist an influenza epidemic or pandemic.

It is yet another object of the present invention to employ such an attenuated live influenza virus which will be safe to employ and act immediately.

It is a further object of the invention to employ a cold-adapted live influenza virus vaccine as an antiviral against influenza.

These and other objects of the invention will be more fully understood from the following description of the invention.

DESCRIPTION OF THE PREFERRED EMBODIMENTS

The term "patient" as used herein refers to members of the animal kingdom, including humans, horses, chickens and other birds.

The terms "immediate" or "immediately" as used herein means acting in a lesser period of time than that required for the patient's body to develop a sufficient level of antibodies as to establish immunity to the influenza.

The present invention centers around a method for effectively and immediately interfering with the growth of influenza virus in a patient. The obvious advantage of this approach over the use of a vaccine is that the patient obtains immediate benefit from the intranasal administration of the material without having to delay benefits until such time as a sufficient level of antibodies can be generated by the patient's immune system to establish immunity. As indicated herein, the antibody generation approach may take about two weeks or more to establish the desired immunity in a human.

In the present invention a prophylactically or therapeutically effective dosage of an attenuated live influenza virus is introduced into the patient intranasally in order to effect immediate interference with the growth of the influenza virus. The influenza virus whose growth is blocked is not limited to the specific influenza virus from which the attenuated live influenza virus has been derived, but will block the growth of numerous other influenza viruses as well.

In the preferred practice of the invention, the method is practiced on a human patient employing an attenuated virus in a solution having an attenuated virus concentration of up to about $10^7$ $EID_{50}$ per milliliter on a volume basis and employing a quantity of said solution of up to about 1 milliliter in the dose administered. The dose may be administered only once, or repeated if the patient's condition warrants.

It is known that the Maassab cold-adapted vaccine strain can be genetically reassorted with a variety of epidemic wild-type viruses to yield reassortants which contain the HA and NA gene segments of the wild-type parent virus. These are the genes that code for the immunizing antigens found on the surface of the virus particle. The reassortants also contain the other six genome segments of the cold-adapted parent that are responsible for the attenuated phenotype in humans and animals. They have also been shown to be safe and effective when used as vaccines in humans.

Unlike the vaccine use, however, in the case of interference the two surface glycoproteins do not play a role. The six genome segments of the cold-adapted parent may be reassorted with a variety of wild-type glycoprotein gene segments. Such reassortants retain the ability to interfere due to the presence of the six genes from the cold-adapted parent.

EXAMPLE 1

Tests were performed employing ferrets as these animals respond with a disease pattern much the same as humans to infection with epidemic influenza virus. The responses typically are a high fever, significant virus replication in the lungs and acute respiratory symptoms. Ferrets were infected simultaneously with an epidemic influenza virus and the live attenuated vaccine. The results of these tests is shown in Table 1. Considering first the A/WA/WT (A/Washington/897/80 [H3N2]) virus which is a type A influenza virus administered at an $EID_{50}$ of $10^7$. Four ferrets which had nasal administration of this virus developed fever with the fever ranging as high as 105° F. and lasting 24 hours. All four of the ferrets experienced acute catarrhal inflammation of the nasal mucous membrane which endured for three days. In the second phase of the report in Table 1, four other ferrets were inoculated intranasally with a combination of A/WA/WT virus and the cold-adapted attenuated reassortant vaccine virus each in the quantities of $10^7$ $EID_{50}$. None of these ferrets so treated developed fever or coryza.

TABLE 1

DOMINANCE OF COLD-ADAPTED VACCINE VIRUS IN FERRETS - CLINICAL RESPONSES

| INOCULUM (I.N.) | $EID_{50}$ ($LOG_{10}$) | NO. FERRETS | FERRETS WITH FEVER | RANGE OF FEVER | DURATION OF FEVER | FERRETS WITH CORYZA | DURATION |
|---|---|---|---|---|---|---|---|
| A/WA/WT | 7.0 | 4 | 4/4 | 105° F. | 24 h | 4/4 | 3 d |
| A/WA/WT + A/WA/CA | 7.0 + 7.0 | 4 | 0/4 | — | — | 0/4 | — |

TABLE 2

DOMINANCE OF COLD-ADAPTED VACCINE VIRUS IN FERRETS - VIRUS REPLICATION

| INOCULUM (I.N.) | $EID_{50}$ ($LOG_{10}$) | NO. FERRETS | TURBINATES* 3 d | TURBINATES* 8 d | LUNG* 3 d | LUNG* 8 d | SHEDDING | PATTERN OF INFECTION |
|---|---|---|---|---|---|---|---|---|
| A/WA/WT | 7.0 | 4 | 7.0 | <1.0 | 2.0 | <1.0 | 3 d | 4/4 WT |
| A/WA/WT + A/WA/CA | 7.0 + 7.0 | 4 | 7.3 | <1.0 | <1.0 | <1.0 | 4 d | 4/4 CA |

*Virus titer expressed as $log_{10}$ of virus per gram of tissue

This shows that administering the A/WA/WT influenza virus alone produced in the experimental patient the classic symptoms of influenza virus type A in all of the ferrets. Simultaneous administration of the influenza virus with the cold-adapted reassortant vaccine virus resulted in no such symptoms. As the vaccine effect of the cold-adapted reassortant vaccine virus in generating antibodies could not have developed immunity to the influenza virus which was introduced simultaneously therewith, it is clear that the cold-adapted reassortant virus served as an antiviral agent to interfere with or block growth of the influenza virus.

Table 2 refers to the pattern of viral replication in the animals described in Table 1. The results show that the animals which received the wild-type virus alone showed a pattern of virus replication typical of an epidemic influenza virus, namely, virus replication in the lungs and turbinates. In contrast, the animals simultaneously infected with both the wild-type virus and the cold-adapted vaccine virus showed a pattern of infection typical of an infection with the cold-adapted vaccine virus alone, namely, virus replication confined to the turbinates. No virus was recovered from the lungs. This is clear evidence that when the cold-adapted virus is given simultaneously with the wild-type virus, the cold-adapted virus prevents the development of disease and prevents the wild-type virus from growing in the lungs.

EXAMPLE 2

The ability to interfere with wild-type viruses is a desirable trait for any live, attenuated vaccine. The cold-adapted reassortant of influenza A virus interferes with the replication of wild-type influenza A in mixed infections of either Madin-Darby Canine Kidney (MDCK) cells or embryonated eggs. The cold adapted strain (ca) of influenza A virus was isolated following 32 passages of a wild-type virus (A/Ann Arbor/6/60), at reduced temperature in primary chick kidney cells. The ca virus acquired the ability to form plaques at 25° C. and has a temperature sensitive (ts) phenotype which restricts its growth at 39.5° C. Genetic reassortment of this virus with a variety of wild-type (wt) viruses yields reassortants which contain the HA and NA segments of the wt parent and the other six genome segments of the ca parent. Such reassortants have an attenuated phenotype in humans and animals and have been shown to be safe and effective vaccines in humans. See Murphy, J. Virol. 62, 488-495 (1981).

In addition to inducing the production of neutralizing antibodies, the ca virus directly inhibits the growth of wt influenza A. In MDCK cells doubly infected with wt influenza A and the ca reassortant virus, the yield of wt virus is reduced by as much as 3,000-fold and the protein synthesis phenotype expressed is that of the ca virus. Interference is detected even when infection with wt virus is carried out at a 9-fold excess or 2 hr before infection with the ca virus. The ability of the ca reassortant to interfere with wt viruses bearing completely unrelated transmembrane glycoproteins indicates that at least two genes (HA and NA) which are surface proteins are not involved in the interference phenomenon.

It has been demonstrated with single gene reassortants that the ca phenotype is specified by the PA gene, while the PB2 and PB1 genes specify the temperature sensitive (ts) phenotype. See Snyder et al. J. Virol 62, 488-495 (1988). The four genes of the ca virus (PA, PB2, PB1 and M) contribute to the attenuation (att) phenotype of the ca virus.

In the following experiments, these reassortants were used to assess the role of the individual ca genes in the dominance (dom) phenotype.

Monolayer cultures of the Madin-Darby line of canine kidney (MDCK) cells were grown in Eagle's minimal essential medium (MEM) supplemented with 10% calf serum containing 100 units/ml penicillin and 100 ug/ml streptomycin. Two wild-type (wt) viruses, A/Washington/897/80 (H3N2) and A/Korea/1/82 (H3N2), their cold-adapted (ca) reassortants A/Washington/897/80 (H3N2) CR-48 and A/Korea/1/82 (H3N2) CR-59 were employed. For simplicity, these viruses will be referred to as A/WA, A/KO, A/WA/ca and A/KO/ca, respectively. The single ca gene reassortant viruses used in this study were derived by crossing the ca prototype virus A/Ann Arbor/6/60 (H2N2) with a wt virus, A/Korea/1/82 (H3N2). The preparation and properties of these reassortants are known to those skilled in the art. See Snyder et al. J. Virol. 62, 488-495 (1988). The single gene reassortants are designated herein by the ca gene they carry. Virus stocks were prepared in embryonated eggs as described below.

Virus yield experiments were performed in monolayers of MDCK cells in 24-well trays. Cells were infected at an m.o.i. of 2 in 0.2ml MEM containing 0.125% bovine serum albumin (BSA) and 1ug/ml DEAE-dextran. After adsorption for 1 hr at 34° C., the inoculum was removed, the monolayers were rinsed three times with phosphate buffered saline (PBS), and refed with MEM containing 0.125% BSA and 1ug/ml TPCK-trypsin. The medium was removed 24 hr after infection and the virus yield determined by plaque assay.

The assay was performed in monolayers of MDCK cells in 60mm dishes as previously described (Whitaker-Dowling et al., 1990), using a double overlay of nutrient and staining agar. The staining agar was added after 3 days of incubation at the appropriate temperature and the plaques were counted 24 hr later. For clonal analysis, well isolated plaques were excised from terminal dilution dishes using a sterile scalpel blade or a Pasteur pipet and placed directly in 24-well trays of MDCK monolayers. Viral proteins were analyzed as described herein below.

Virus inocula ($10^4$pfu/0.1 ml PBS) were injected into the allantoic sac of 10- or 11-day old embryonated eggs. After 48 hr at 34° C., allantoic fluids were harvested, clarified by low speed centrifugation, and assayed for infectivity.

Monolayer cultures of MDCK cells in 24-well trays were singly or doubly infected with the indicated viruses at an m.o.i. of 2. After 24 hr at 34° C., the cells were radiolabeled with [$^{35}$S]-methionine for 2 hr, a cell lysate prepared and the viral proteins analyzed by SDS-PAGE as previously described. When excised plaques were used as inoculum, the monolayers were examined by light microscopy and radiolabeled for 2 hr at the first sign of virus-induced cytopathology, usually between 24 and 48 hr after addition of the agar plug to the well.

MDCK cells in 24-well trays were singly or doubly infected with wt A/KO, A/KO/ca reassortant virus (6 ca genes + 2 wt genes, HA AND NA), or single ca gene reassortant viruses (1 ca gene + 7 wt A/KO genes). At 24hr after infections the culture fluid was harvested for analysis of progeny virus and the cells were labeled for 2 hr with [$^{35}$S] methionine to examine viral protein synthesis. It is important to note that 4 of the 6 single ca gene reassortants encoded proteins can be distinguished from their wt counterparts by SDS-PAGE, namely, PA, NP, M1 and NS1. These migration differences can be used to test the ability of the single ca gene reassortants to dominate at the level of protein synthesis. In mixed infections with wt virus, the single gene reassortant carrying segment 7 (M) derived from the ca virus is dominant in regard to the synthesis of the M1 protein. In contrast the 2 single gene reassortants carrying the ca PA or the ca NS gene are co-dominant, i.e., both st temperature sensitive and ca proteins are expressed in mixed infection. Expression of the NP protein of the ca virus is recessive in mixed infection. The other 2 single ca gene reassortants, PB1 and PB2, could not be differentiated from wt by SDS-PAGE.

In addition to determining protein synthesis phenotypes, virus yields from the mixed infections were also analyzed. because of their ts phenotype, it was possible to assess the dominance of the PB1, PB2, and NP single ca gene reassortants by measuring the efficiency of plating of the mixed yields at the permissive and nonpermissive temperatures. None of these reassortants significantly inhibited the growth of wt virus in mixed infections (Table 3) In the case of the PB1 and PB2 reassortants, the composition of the progeny virus roughly reflected the ratio of the input viruses. However, when cells were doubly infected with wt and the NP single gene reassortant, 95% of the progeny were wt virus. These results are consistent with the dominance of wt protein synthesis in mixed infection with the NP single ca gene reassortant observed.

The other three single ca gene reassortants (PA, M, and NS) could not be differentiated from wt in mixed yields by determining efficiency of plating at 34° C. and 39.5° C., as they are not ts viruses. However, the proteins encoded by each of these ca genes could be distinguished from their wt counterparts by SDS-PAGE. In order to determine the ability of the ca PA, M, and NS single gene reassortants to interfere, the amount of virus produced during mixed infection with wt A/KO virus was measured by plaque assay and the contribution of each of the two input viruses to the progeny was determined by analysis of the protein synthesis phenotype of clonal isolates (Table 4). Coinfection with the reassortant containing the ca M gene reduced the yield of wt virus, 1,110-fold, which is similar to the level of interference produced by the parental ca vaccine strain (Table 3). Furthermore, the majority of the progeny virus in the mixed yield had the protein synthesis phenotype of the ca single gene M reassortant. The reassortants carrying the ca PA and NS genes failed to produce a significant inhibition of wt virus yield.

Embryonated eggs were singly or doubly infected with wt A/KO, A/KO/ca, and the single ca gene reassortants and incubated at 34° C. An inoculum of 10⁴ PFU per egg of each virus was used. Allantoic fluids were harvested 48 hr after infection and, in the case of the ts PB1 and PB2 single ca gene reassortants, assayed for plaque-forming units (PFU) at 34° C. and 39.5° C. (Table 5). Neither of these single ca gene reassortants inhibited wt virus yield in mixed infection. When the non-temperature sensitive single ca gene reassortants (PA, M, and NS) were used in mixed infections in eggs and the progeny scored by clonal analysis of protein synthesis phenotype, it was apparent that only the single gene reassortant containing segment 7(M) of the ca virus inhibited wt virus (Table 6). As none of the 30 clones tested from the yield of this mixed infection produced a wt M1 protein, it was not possible to calculate with accuracy the full extent of the inhibition of wt virus. The single ca NP reassortant grown in embryonated eggs lost its ts phenotype, most likely as a result of reversion during the multiple rounds of replication in this host. Furthermore, the wt and ca NP proteins from the clones recovered from single and mixed infections in embryonated eggs could not be differentiated by SDS-PAGE.

Since it was likely that mixed infections with wt and ca viruses would produce reassortants, it followed that those reassortants which contained the gene(s) responsible

TABLE 3

INTERFERENCE BY SINGLE CA GENE REASSORTANTS (PB1, PB2, NP) IN MDCK CELLS

| VIRUS[a] | PFU/ML[b] 34° C. | (Log$_{10}$) 39.5° C. | FOLD-INHIBITION[c] | % YIELD THAT IS WT[d] |
|---|---|---|---|---|
| A/KO | 7.1 | 6.2 | | |
| A/KO/ca | 4.9 | <3.0 | | |
| MIX | 4.7 | 3.0 | 1360 | 18 |
| PB1 | 6.5 | <3.0 | | |
| A/KOxPB1 | 6.8 | 5.7 | 3 | 60 |
| PB2 | 6.5 | <3.0 | | |
| A/KOxPB2 | 6.6 | 5.2 | 9 | 30 |
| NP | 6.3 | <3.0 | | |
| A/KOxNP | 6.4 | 5.5 | 5 | 95 |

[a]MDCK cells were infected at 34° C. The fluids were harvested 24 hr after infection and assayed for PFU at the two temperatures.
[b]Plaque-forming units/ml
[c]Fold-inhibition = $\frac{\text{Yield of ts + virus from singly infected cells}}{\text{Yield of ts + virus from doubly infected cells}}$
[d]% yield that is wild-type = $\frac{\text{Mixed yield at 39.5°}}{\text{Mixed yield at 34°} \times \text{wt yield at 39.5°/34°}} \times 100$

TABLE 5

INTERFERENCE BY SINGLE CA GENE REASSORTANTS (PB1, PB2) IN EMBRYONATED EGGS

| VIRUS[a] | PFU/ML (Log$_{10}$) 34° | 39.5° | FOLD-INHIBITION[b] | % YIELD THAT IS WT[c] |
|---|---|---|---|---|
| A/KO | 7.3 | 7.0 | | |
| A/KO/ca | 6.8 | <3.0 | | |
| MIX | 7.0 | 5.3 | 55 | 3 |
| PB1 | 7.1 | <3.0 | | |
| A/KO × PB1 | 7.1 | 6.8 | 2 | 100 |
| PB2 | 7.2 | <3.0 | | |
| A/KO × PB2 | 7.2 | 7.1 | 0 | 100 |

[a]Embryonated eggs were singly or doubly infected with 10⁴ PFU of each virus and incubated at 34°. Allantoic fluids were harvested 48 hr after infection and assayed for PFU at the two temperatures.
[b]See footnote Table 1.
[c]See footnote Table 1.

TABLE 4

INTERFERENCE BY SINGLE CA GENE REASSORTANTS (PA, M, NS) IN MDCK CELLS

| VIRUS[a] | PFU/ML at 34° (Log$_{10}$) | WT CLONES / TOTAL CLONES[b] | FOLD-INHIBITION[c] | % YIELD THAT IS WT[d] |
|---|---|---|---|---|
| A/KO | 7.1 | | | |
| PA | 6.8 | | | |
| A/KOxPA | 6.7 | 3/26 | 20 | 12 |
| M | 4.9 | | | |
| A/KOxM | 5.4 | 1/27 | 1110 | 4 |
| NS | 7.1 | | | |
| A/KOxNS | 6.8 | 11/30 | 5 | 37 |

[a]MDCK cells were infected at 34°. The fluids were harvested 24 hr after infection and assayed for PFU at 34°.
[b]Clones were selected from terminal dilution plates of mixed infection assays and wt or ca phenotype determined by SDS-PAGE as described in the text and shown in FIG. 2.
[c]Fold-inhibition = $\frac{\text{Yield of wt virus (A/KO)}}{\text{Mixed yield} \times \text{% yield that is wt}}$
[d]% yield that is wt = $\frac{\text{wt clones}}{\text{total clones}} \times 100$

TABLE 6

INTERFERENCE BY SINGLE CA GENE REASSORTANTS (PA, M, NS) IN EMBRYONATED EGGS

| VIRUS[a] | PFU/ML at 34° ($Log_{10}$) | WT CLONES / TOTAL CLONES[b] | FOLD-INHIBITION[c] | % YIELD THAT IS WT[d] |
|---|---|---|---|---|
| A/KO | 7.3 | | | |
| PA | 7.9 | | | |
| A/KOxPA | 7.7 | 10/29 | 0 | 35 |
| M | 8.1 | | | |
| A/KOxM | 7.6 | 0/31 | 17 | <3 |
| NS | 7.8 | | | |
| A/KOxNS | 8.0 | 3/63 | 4 | 5 |

[a]Embryonated eggs were singly or doubly infected with $10^4$PFU of each virus and incubated at 34°. Allantoic fluids were harvested 48 hr after infection and assayed for PFU at 34°.
[b]See footnote Table 2.
[c]See footnote Table 2.
[d]See footnote Table 2.

On the basis of previous findings that the ability of the ca virus to dominate in mixed infection was not temperature-sensitive single virus plaques were randomly selected at 39.5° C. from the third serial passage at 34° C. of a mixed infection of A/WA and A/WA/ca The protein synthesis phenotype of the progeny from each clone was analyzed by SDS-PAGE. Of the 12 clones isolated, 6 clones proved to be reassortants that produced an M1 protein characteristic of the ca virus and, therefore, contained segment (M) derived from the ca virus. In addition to the ca M1 protein, 2 of the 6 reassortant clones also produced other proteins (PA, NP and NS1) derived from the ca virus. It should be noted that in each instance these proteins always accompanied the M1 protein of the ca parental virus.

To test if the reassortants possessed the ability to dominate in mixed infection, virus stocks were prepared in MDCK cells from reassortants that produced only an M1 protein derived from the ca virus. MDCK cells were singly or doubly infected with wt virus and three reassortant clones and their ability to dominate at the level of protein synthesis was examined. The protein synthesis patterns clearly demonstrated that all 3 reassortant clones that produce the ca M1 protein were dominant in mixed infections with wt A/WA virus. Taken together, these findings were considered additional evidence that segment 7 (M) of the ca virus encodes the dominance function.

It is clear from the evidence presented that segment 7 (M) is responsible for the ability of ca reassortant virus to interfere with the replication of wt virus in MDCK cells and in embryonated eggs. This conclusion is based on the results of several different experiments. When single ca gene reassortants were tested for their ability to interfere with the growth of wt virus in MDCK cells, it was apparent that the reassortant carrying the ca segment 7 (M) was dominant over wt virus. This dominance was evident at the level of both virus gene expression and virus yield. It is interesting to note the relationship between permissiveness of the host system for the ca virus and its ability to interfere. In MDCK cells the interference occurs under conditions which are less than optimum for the growth of the ca virus. When one compares the virus titers achieved in MDCK cells infected with A/KO/ca virus alone with those obtained in mixed infections of wt A/KO and A/KO/ca (Table 3) it is apparent that the total yield is reduced to the level achieved by the ca virus alone. This phenotype of growth restriction in MDCK cells is associated with segment 7 (M) of the ca virus (Table 4). However, a restricted pattern of growth does not completely explain the dominance of the ca virus. Under conditions that are permissive for the ca virus, i.e., in embryonated eggs, the dominance of the ca virus, although reduced, is still apparent (Table 5). It is not clear how much of this reduction is due to the efficient replication of the ca virus in eggs. Another possible explanation for the reduced level of inhibition of wt virus in eggs is the low input multiplicity used for infection. This would permit a high proportion of singly infected cells during the initial rounds of replication in the allantoic sac, thus protecting the wt virus from interference.

It is possible that gene segments other than segments 7 may contribute in a minor way to the dom phenotype. In MDCK cells the single gene reassortant carrying the ca PA gene caused a reduction of wt virus yield (20-fold) which was much less than the inhibition by the ca M reassortant (1,110-fold). In embryonated eggs, the single ca NS gene reassortant caused only a 4-fold inhibition of wt yield but the proportion of the yield that was wt virus was only 5%. However, in this case the reduction is more apparent than real since the single ca NS gene reassortant alone grew more efficiently in embryonated eggs than did wt virus (Table 6). This growth advantage of the ca NS reassortant is a characteristic easily distinguished from the ability to interfere. Minor as it might be, a contribution of ca genes other than the M gene to the dom phenotype would not be without precedent. Snyder et al., J. Virol 62, 488–495 (1988) in their investigations of the att phenotype found that in different hosts a varying constellation of ca genes was involved in the att phenotype. In ferrets a combination of the PB1, PB2, PA, and M ca genes was responsible for the restriction of virus replication in the lower respiratory tract, whereas in hamsters the ca PB1 gene played a minor role in attenuation and the ca PA gene was not involved at all. In the case of humans, they reported that only the PA and M genes from the ca donor virus contributed to the att phenotype. However, because of their role in the ts phenotype, Snyder and his colleagues inferred that the ca PB1 and PB2 genes also may contribute to the att phenotype in humans by limiting viral growth in the lower respiratory tract.

Another line of evidence for the importance of the ca segment 7 in the dom phenotype was obtained by serial passage in MDCK cells of the progeny of a mixed infection by a wt virus and its ca reassortant vaccine virus. These serial passages selected a virus population that contained a high proportion of reassortants carrying the M gene of the ca parental strain. Furthermore, when these ca M reassortants were used in mixed infections, they were dominant over wt virus. This finding lends additional support to the central role of the ca M gene in the dom phenotype. It is important to note that the ca M gene segment also confers attenuation, thereby linking the att and dom phenotypes. The ca virus dom phenotype being expressed in the human respiratory tract as it is in cell cultures and embryonated eggs, the selective pressure during coinfection with epidemic strains would always favor attenuated viruses. Thus, the linkage between the att and dom phenotypes would confer an additional safety factor on this live virus vaccine.

It is difficult to determine with certainty the specific mechanism by which the ca M gene plays a central role in the dom phenotype, a phenotype that is characterized by interference with wt virus growth at the level of gene expression. Sequence analysis of the ca M gene revealed a single base change which results in an amino acid substitution at position 86 of the M2 protein. The role of the M2 protein in the replication cycle of influenza virus has not been completely defined. It is known that the M2 protein is expressed abundantly at the cell surface but is largely excluded from virions. In addition, M2 is believed to be involved in the initiation of infections since amantadine-resistant mutants are altered in the M2 gene. The antibody binding to the M2 protein of a sensitive influenza virus interferes with a direct or indirect interaction of the cytoplasmic domain of M2 with the M1 protein. In attempting to determine the possible functions of the M2 protein, it has been suggested that one of the major roles for the M2 protein might be in "chaperoning" M1 protein in its transport to the cell membrane and/or in the maturation of virus particles. It is possible that an alteration of the ca M2 protein which affected its ability to interact with the M1 protein is capable of binding to single-stranded RNAs and that this protein also can inhibit in vitro transcription by influenza viral cores. Direct evidence to support this analysis of the role of the M2 protein is not available at present.

These cell tests, therefore, show that the cold-adapted attenuated reassortant influenza virus has a direct and immediate effect in interfering with the replication of influenza virus. The tests further provide enhanced understanding of the genetic mechanism by which this is accomplished.

Segment 7 (M) of the cold-adapted live influenza A virus vaccine plays a primary role in the ability of this of this virus to interfere with the replication of wild-type influenza A viruses. This conclusion is based on several lines of evidence. Single gene reassortant viruses derived by crossing influenza A/Ann Arbor/6/60 (H2N2) cold-adapted donor virus with an epidemic wild-type strain, A/Korea/1/82 (H3N2) (See Snyder et al., J. Virol. 62:488-495, 1988), were tested for their ability to interfere with wild-type parental virus in MDCK cells and embryonated eggs. It was apparent in both hosts that the single gene reassortant carrying segment 7 (M) derived from the cold-adapted virus was dominant over wild-type virus. Additional confirmation of the role of segment 7(M) in trans-dominance of the cold-adapted vaccine virus was derived from the analysis of reassortants produced by mixed infection by a wild-type virus and its cold-adapted reassortant vaccine strain. After three serial passages, the virus yield contained a high proportion of reassortants carrying segment 7 (M) of the cold-adapted parental strain. When used in mixed infections, these reassortants were dominant over the replication of the parental wild-type virus.

As will be apparent from the foregoing, the intranasal administration of attenuated reassortant live influenza virus produced immediate interference with the growth of the influenza virus, whereas, the vaccine aspect produced benefits only after a period of eight days. This results in the conclusion that the method of the present invention is an effective means of extinguishing an epidemic and bringing about immediate cure of influenza by means of the interfering effect of the cold-adapted virus without requiring the patient to await the period of time which must elapse before immunity is established through antibodies.

It will be appreciated, therefore, that the present invention has provided a safe and efficient means for preventing development of disease in patients who have just been exposed to, or is about to be exposed to epidemic influenza virus.

In view of the ability of the cold-adapted attenuated live virus vaccine to grow at 25° C. and the impaired capacity to reproduce at 41° C. it will be appreciated that the method of this invention will tend to be more effective against the influenza sought to be destroyed when it is in the nasal passageways then when it has reached the lungs, as the lungs have a higher temperature. It is preferred to employ this method prior to entry of the influenza into the lungs.

For convenience of reference herein, disclosure has centered around the use of epidemic influenza type A virus, as this is a very common strain, as the source of the cold-adapted attenuated virus and may be the type sought to be attacked in the process of this invention. It will be appreciated that other types of influenza virus, such as type B, for example, may be employed as the source material and be attacked by the cold-adapted virus.

For example, tests in MDCK cells have shown that cold-adapted influenza A vaccine virus also interferes with the growth of avian influenza A virus. Also, the cold-adapted influenza A vaccine virus interferes with influenza B virus in MDCK cells and embryonated eggs. The cold-adapted influenza B virus interferes with influenza B virus in MDCK cells.

It will be appreciated that the method of the present invention involves use of the cold-adapted live influenza virus vaccine as an antiviral agent against the influenza, rather than as a vaccine, which would involve substantial elapsed time (which may be on the order of 15 days) to create immunity by antibody production. The method is particularly useful in terminating an epidemic or pandemic outbreak. For example, if an epidemic were to begin to occur in a senior citizen's home, it would be too late to attempt to extinguish the epidemic by vaccination as the influenza would spread too rapidly to make this approach effective. The method of the present invention, however, could be employed to interfere with influenza spread in an immediate manner through action as an antiviral agent.

Use of vaccine requires a determination of the specific strain of influenza which will occur and inoculation in advance of onset. In the event of a "shift" in the influenza strain, the vaccination will not prevent patients from getting the shifted strain. As the method of the present invention, however, has the ability to interfere with influenza viruses of not only the virus from which the cold-activated live influenza virus was derived, but others as well, the method may be employed to resist a pandemic.

Whereas particular embodiments of the invention have been described above for purposes of illustration, it will be appreciated by those skilled in the art that numerous variations of the details may be made without departing from the invention as described in the appended claims.

I claim:

1. A method of treating a patient for influenza virus comprising
introducing as an antiviral agent a cold-adapted reassortant live influenza virus vaccine into said patient intranasally, and
effecting by said introduction immediate interference with the growth of said influenza virus, whereby said interference with the growth of said influenza virus will be achieved without awaiting the body's production of antibodies to said influenza virus.

2. The method of claim 1 including
treating a human patient with said process.

3. The method of claim 2 including
employing said attenuated virus in a solution having an attenuated virus concentration up to about $10^7$ $EID_{50}$ per milliliter on a volume basis.

4. The method of claim 3 including
employing a quantity of said solution of up to about one milliliter per dose.

5. The method of claim 4 including
administering said dosage only once.

6. The method of claim 1 including
effecting said treatment without the two surface glycoproteins of said cold-adapted vaccine being employed in said growth interference.

7. The method of claim 6 including
employing said method to interfere with growth of the virus from which said attenuated live reassortant was derived and at least one other influenza virus not related to said attenuated live reassortant influenza virus from which said reassortant virus was derived.

8. The method of claim 1 including
employing as said attenuated live influenza virus a cold-adapted reassortant of influenza A virus.

9. The method of claim 1 including
employing as said attenuated live influenza virus a cold-adapted reassortant of influenza B virus.

10. The method of claim 6 including
employing attenuated virus carrying segment 7(M) in effecting said immediate interference.

11. The method of claim 1 including
employing said method to prevent growth of said influenza virus in the lungs of said patient.

12. The method of claim 6 including
employing the six reassorted genome segments of said cold-adapted virus in effecting said growth interference.

13. The method of claim 1 including
employing said method to treat prophylactically a patient who has not been exposed to said influenza.

14. The method of claim 1 including
employing said method to treat therapeutically a patient who has been exposed to said influenza.

15. The method of claim 14 including
employing said method prior to entry of said influenza into said patient's lungs.

* * * * *

UNITED STATES PATENT AND TRADEMARK OFFICE
CERTIFICATE OF CORRECTION

PATENT NO. : 5,149,531
DATED : September 22, 1992
INVENTOR(S) : Julius S. Youngner and Patricia W. Dowling It is certified that error appears in the above-indentified patent and that said Letters Patent is hereby corrected as shown below:

Column 2, line 22, "107" should be -- $10^7$ --.

Column 2, line 23, "EID50" should be -- $EID_{50}$ --.

Column 2, line 24, "I" should be --1--.

Column 8, line 3, "104" should be -- $10^4$ --.

Signed and Sealed this

Second Day of May, 1995

Attest:

BRUCE LEHMAN

Attesting Officer    Commissioner of Patents and Trademarks